United States Patent [19]

Neumann et al.

[11] Patent Number: 5,244,789
[45] Date of Patent: Sep. 14, 1993

[54] PROCESS FOR THE DETERMINATION OF PHOSPHOLIPASE A IN BODY FLUIDS

[75] Inventors: Ulrich Neumann, Weilheim; Gudrun Schmidt, Bernried; Martina Junius-Comer, Iffeldorf, all of Fed. Rep. of Germany

[73] Assignee: Boehringer Mannheim GmbH, Mannheim, Fed. Rep. of Germany

[21] Appl. No.: 756,712

[22] Filed: Sep. 9, 1991

[30] Foreign Application Priority Data

Sep. 20, 1990 [DE] Fed. Rep. of Germany ....... 4029845

[51] Int. Cl.$^5$ .............................................. C12Q 1/44
[52] U.S. Cl. ...................................... 435/21; 435/19; 424/2; 424/7.1
[58] Field of Search .................................. 435/19, 21

[56] References Cited

U.S. PATENT DOCUMENTS 4,988,497  1/1991  Neumann et al. .................... 435/19

FOREIGN PATENT DOCUMENTS 0337005 10/1989 European Pat. Off. .
0399379 11/1990 European Pat. Off. .

*Primary Examiner*—Ronald W. Griffin
*Assistant Examiner*—Pamela S. Webber
*Attorney, Agent, or Firm*—Nikaido, Marmelstein, Murray & Oram

[57] ABSTRACT

The present invention provides a process for the determination of phospholipase A in body fluids, wherein the body fluid is incubated with a mixture containing a substrate having a fatty acid residue for the phospholipase and at least two emulsifiers of different chemical classes, namely, at least one neutral emulsifier and a bile acid salt, and the amount of the free fatty acids formed by the cleavage of the substrate is determined in known manner.

18 Claims, No Drawings

PROCESS FOR THE DETERMINATION OF PHOSPHOLIPASE A IN BODY FLUIDS

The present invention is concerned with a process for the determination of phospholipase A in body fluids and especially in serum.

Phospholipases occur ubiquitously in nature in the most varied organisms, those from bee venom and the various snake venoms being especially well known.

The determination of phospholipase A (PLA) can, according to the literature, serve for the diagnosis of various life-endangering diseases. The division of the phospholipases takes place according to point of action on the lecithin molecule. Phospholipase A cleaves the ester bond with the fatty acid molecule, phospholipase $A_1$ cleaving the a-positioned bond and phospholipase $A_2$ the $\beta$-positioned bond.

In the human pancreas, PLA is formed in considerable amounts and secreted into the duodenum where, per day, about 4 g of nutrient lecithin and, in addition, about 10 g of the body's own lecithin are cleaved. With about 130 amino acids, pancreatic PLA is an extremely small enzyme.

Quite some time ago, an investigation was made for the clinical relevance of PLA such as is possessed by the other pancreatic enzymes lipase and amylase. Because of the dangerousness of various PLA enzymes (due to the action of $PLA_2$ on lecithins, by the splitting off of a fatty acid in the 2-position, the highly toxic lysolecithins result), there was considered, in particular, the possibility of a differentiation of the degree of severity of pancreatitis. Acute pancreatitis can, namely, be present as a relatively harmless oedematous form or as an extremely dangerous necrosing form, the differential diagnosis of which is clinically very important. Hoffmann et al. (J. Clin. Chem. Clin. Biochem., 23, 582/1985) were able to show, on the basis of about 50 sera with clinically ascertained diagnosis, that, in the case of acute haemorrhargic pancreatitis, a prognosis regarding the course of severity of the disease can be made via the PLA enzyme activity. By means of further investigational material, in the course of time it became clear that other diseases are also involved with an increase of the PLA, the PLA level here, too, also always being an indicator of the severity of the disease. By way of example, there are here mentioned lung failure, ARDS (see MacGuire et al., J. Clin. Invest., 69, 543-553/1982), sepsis (see P. Vadas, J. Lab. Clin. Med., 104, 873/1984), allergic shock, progressive chronic polyarthritis (see Pruzanski et al., J. Rheumatol., 12, 211/1985), as well as bronchial asthma.

In the case of these aspects of disease, it was obvious that the cause could not be brought into conjunction with a pancreatic PLA. It has been reported that from the synovial liquid of a patient with progressive chronic polyarthritis, a PLA has been isolated which does not react immunologically with an antiserum against the human pancreatic PLA. Hoffmann et al. were able to show that the PLA in human sera has a pH optimum different from that of the human pancreatic PLA (see Dt. Ges. f. Klin. Chemie e.V.-Communications 5/87, 226/1987).

The first test for PLA in human sera was described by Zieve and Vogel (see J. Lab. Clin. Invest., 57, 586/1961). It was a titrimetric test which, per determination, required an incubation time of 18 hours at a temperature of 55° C. Subsequently, further PLA determination methods were published, such as measurement via radioactively-labelled substrates, extraction and photometry of the free fatty acids formed, fluorimetry and the like. However, it is common to all of these methods that they are extremely time-consuming and complicated so that a routine carrying out is not possible.

Therefore, it is an object of the present invention to provide a PLA test which avoids the analytical and apparatus problems of the known PLA tests and which can be carried out with a conventional laboratory photometer.

Thus, according to the present invention, there is provided a process for the determination of phospholipase A (PLA) in body fluids and especially in serum, wherein the body fluid to be tested is incubated with a mixture containing a substrate having a fatty acid residue for the phospholipase and at least two emulsifiers of different chemical classes, namely, at least one neutral emulsifier and a bile acid salt, and the amount of free fatty acids formed by cleavage of the substrate is determined in known manner.

In the process according to the present invention, the neutral emulsifier can be hydrophilic or also lipophilic.

As substrate, there can be used natural lecithin but not all lecithins are of equal suitability. A high proportion of unsaturated fatty acids in the lecithin molecule appears to be a requisite for a good test result. In a preferred embodiment of the present invention, use is made of a natural lecithin substrate from soya beans or of Lipoid S20 (a commercially available soy bean lecithin).

Apart from natural lecithin, synthetic substrates can also be used which correspond to the general formula:

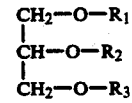

wherein $R_1$ and $R_2$ are alkyl radicals containing up to 20 carbon atoms or carbonyl radicals containing up to 20 carbon atoms, with the proviso that at least one of the two radicals is a carbonyl radical, and $R_3$ is $-SO_3H$.

In a preferred embodiment of the present invention, the first emulsifier is an alkyl glucoside, a polyether, dimethyl sulphoxide (DMSO) or Triton® X-100 (alkylphenyl polyethylene glycol). As the second emulsifier, there is used a bile acid salt, preferably a taurodesoxycholate or a desoxycholate. Especially preferably, there is used a combination of taurodesoxycholate with octyl-$\beta$-D-glucopyranoside, polyoxyethylene ether, DMSO or Triton® X-100.

In the process according to the present invention, there is preferably used a lyophilised substrate which is dissolved in a buffer and especially in HEPES buffer. In this way, it is made easy to employ standardised amounts of substrate, the measurement of the amount being especially simple.

The determination of the free fatty acids formed can, in principle, take place in different ways, namely, in principle by the reaction of the free fatty acid in the presence of coenzyme A and ATP by acyl-CoA synthetase to give acyl-CoA, AMP and pyrophosphate and detection of one of the components formed. There is hereby conceivable not only the determination via acyl-CoA, in which the acyl-CoA is reacted by acyl-CoA oxidase in the presence of oxygen to give 2,3-transenoyl-CoA and hydrogen peroxide and the hydrogen peroxide formed is detected via a colored material formation reaction in the presence of peroxidase. Another possibility is the determination via the pyrophosphate (PPi) formed. In this case, PPi is reacted by a series of enzymatically-catalysed reactions to give gluconate-6-phosphate. A further possibility, which is preferred for the process according to the present invention, is the determination via the AMP formed. AMP is hereby reacted in the presence of ATP by myokinase to give ADP which in turn is reacted in the presence of phosphoenol pyruvate by pyruvate kinase to give ATP and pyruvate, whereafter the pyruvate formed is converted in the presence of NADH by lactate dehydrogenase into lactate and NAD. The determination takes place by measurement of the change of extinction by the addition of the PLA-containing body fluid to the substrate and emulsifier-containing mixture, which preferably also contains, at the same time, the reagents for the further reactions of AMP to lactate. In comparison with a calibration curve, which has been produced with a known amount of PLA, the concentration in the body fluid can then be determined.

In yet another preferred embodiment of the present invention, the determination of the fatty acids formed is carried out in the presence of triethanolamine hydrochloride buffer.

In order to bring about a further simplification of the process, in the carrying out of the test, a clarifying system is preferably added which does not impair the color formation. In an especially preferred embodiment, for this purpose Triton ® X-100 is added if this has not already been used as emulsifier.

With the carrying out of the process according to the present invention, it is possible to determine the amount of PLA in body fluids in a simple and routine manner. In particular, this method can easily be carried out with the use of an automatic analyser, which very considerably simplifies the use of the process in a clinical laboratory.

The following Examples are given for the purpose of illustrating the present invention.

Abbreviations:
DMSO: dimethyl sulphoxide
TDCh: taurodesoxycholate
PEP: phosphoenol pyruvate
PK: pyruvate kinase
LDH: lactate dehydrogenase
ACS: acyl coenzyme A synthetase
NaDCh: sodium desoxycholate

EXAMPLE 1

Preparation of the Emulsion

Emulsifiers 1.1. Octyl glucoside.

35 mg of lecithin from soya beans are stirred for about 2 hours with 4.25 ml HEPES buffer (pH 7.9, 100 mmol/l), 0.250 ml TDCh solution (120 mmol/l), 0.250 ml of a solution of calcium and magnesium ions (200 and 400 mmol/l, respectively), as well as 0.250 ml octyl glucoside solution (100 mmol/l). Subsequently, the emulsion is diluted 2+1 with octyl glucoside solution. The extinction of the emulsion is measured at 365 nm against air. It amounts to 1.456.

Test Batch

The determinations are carried out at 37° C. Measurement is made at a wavelength of 365 nm against air.

To 750 μl of the above-mentioned solution are added 25 μl of a CoA solution (90 mmol/l), 75 μl of a coenzyme solution (ATP: 145 mmol/l ; PEP: 55 mmol/l ; NADH: 9.4 mmol/l), as well as 50 μl of an enzyme solution (myokinase: 165 kU/l; LDH: 377 kU/l; PK: 141 kU/l ; ACS: 5.6 kU/l). As sample, there are used 50 μl of a PLA-containing human serum.

1.2. Brij ® 35 (polyethyleneglycol dodecyl ether).

35 mg lecithin are mixed with 0.250 ml taurodesoxycholate solution and 4.5 ml HEPES buffer (pH 7.9, 100 mmol/l) and stirred with gentle warming. After 30 minutes, 0.250 ml of a solution of calcium and magnesium ions (200 mmol/l and 400 mmol/l , respectively) are added thereto, as well as 0.250 ml Brij ® 35 solution (200 g/l). The emulsion is subsequently diluted with HEPES buffer (2 parts of emulsion and 1 part of buffer). The extinction of the emulsion at 365 nm against air is 2.243. The test batch is carried out as described in 1.1.

1.3. Dimethyl sulphoxide (DMSO).

35 mg lecithin are stirred with 4.5 ml HEPES buffer (pH 7.9, 100 mmol/l) and 0.250 ml taurodesoxycholate solution and subsequently mixed with 0.250 ml of a solution of calcium and magnesium ions (200 mmol/l and 400 mmol/l, respectively). Subsequently, the emulsion is mixed with 2 μl DMSO solution (concentration in the emulsion: 5 mmol/l). The extinction of the emulsion at 365 nm against air is 2.573.

2 ml of emulsion are mixed with 0.100 ml of a solution of 200 mmol/l calcium chloride dihydrate, 400 mmol/l magnesium chloride hexahydrate and 200 mmol/l Triton ® X-100. The extinction of the emulsion at 365 nm against air is 1.320. The test batch is carried out as described in 1.1.

EXAMPLE 2

PLA Substrate 2.1. PLA substrate:

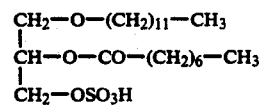

Preparation of the Emulsion

The PLA substrate is mixed with 1.5 ml of a solution of 125 mmol/l TRIS/HCl, 4 mmol/l calcium chloride, 50 mmol/l mannitol, 1 mmol/l NaDCh and 4 mmol/l Triton ® X-100. The substrate concentration is 17 mmol/l. The emulsion is stirred for 1 hour at ambient temperature using a magnetic stirrer. The extinction of the emulsion is measured at 365 nm against air. It is 1.851.

Test Batch a) Incubation Batch

250 μl of the above-mentioned emulsion are incubated with 50 μl of sample. After 5 and 20 minutes, respectively, in each case 50 μl are removed and pipetted into 50 μl of a stop solution. The incubation takes place at 37° C.

b) Determination Batch

Wavelength 546 nm against air
temperature: 37° C.

To 1000 μl reagent solution A (ATP, acyl-CoA synthetase, peroxidase, ascorbate oxidase and 4-amino-antipyrine) are added 100 μl of sample. After 10 minutes, 50 μl of reagent solution B (N-ethylmaleinimide, acyl-CoA oxidase) are added thereto. After a further 10 minutes, the extinction is measured. The PLA activity is given from the difference.

With the substrate, there is achieved a very good recovery of the PLA activity (130%) in PLA human serum in comparison with soya bean lecithin as substrate. The recovery of hog pancreatic PLA is 52.9%.

2.2.1. Determination in the presence of triethanolamine-buffer

The emulsion as prepared in the example 2.1 is lyophilized and dissolved with 5.00 ml of an 100 mmol/l triethanolamine-hydrochlorid buffer, pH=7,8, which additionally contains 2,16 mg ACS, 4,34 mg CoA and 20,82 mg ATP (in 5 ml).

Test Batch

To 500 μl of this solution are added 100 μl of the sample and hold at 37° C. After 5 min 200 μl of this reagent is added to 1000 μl reagent solution A (POD, 4-Aminoantipyrin), 50 μl Solution B (N-ethylmaleinimide, acyl-CoA-oxidase) and 500 μl of a 0.5% Triton X100 solution. The extinction is measured after 10 min at 365 nm against air. The procedure will be repeated after 20 min. From the difference of the extinktions the PLA-activity is calculated.

2.2. PLA substrate:

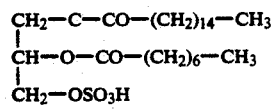

Preparation of the Emulsion a) As described in Example 1. The extinction of the emulsion at 365 nm against air is 2.082.

b) The above-described substrate (end concentration: 12 mmol/l) is mixed with 1.35 ml HEPES buffer (100 mmol/l, pH 7.9) and 0.075 ml of 120 mmol/l taurodesoxycholate solution is subsequently added thereto. The mixture is stirred for 30 minutes with gentle warming, using a magnetic stirrer. To this emulsion are added 0.075 ml of a solution of 200 mmol/l calcium chloride dihydrate, 200 mmol/l Triton ® X-100 and 400 mmol/l magnesium chloride hexahydrate. A clear emulsion is obtained with an extinction of 0.222 measured at 365 nm against air.

Test Batch

As described in Example 1.

The substrate can be used for the detection of hog pancreatic PLA and of serum PLA. The hog pancreatic PLA is recovered at a lower level than the human serum PLA.

2.3. PLA substrate:

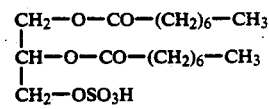

Preparation of the Emulsion a) As described in Example 1. The extinction of the emulsion is 0.605.

b) As described in Example 2 b). In both cases, the substrate concentration is 12 mmol/l.

Test Batch

As described in Example 1.

The substrate can be used for the detection of hog pancreatic PLA and of human serum PLA, the hog pancreatic PLA being recovered at a lower level than serum PLA.

2.4. PLA substrate.

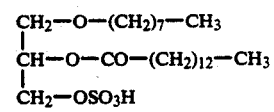

Preparation of the Emulsion

As described in Example 1.

Test Batch

As described in Example 1.
The substrate can be used as a PLA substrate.

EXAMPLE 3.

Lecithins

The following lecithins were investigated with regard to the suitability thereof as PLA substrate: lecithin from soya beans, Roth, Karlsruhe, Germany, No. 9812 lecithin from eggs, Merck, Darmstadt, Germany, No. 5331 lecithin ex cerebro, Roth Karlsruhe, Germany, No. 5957 lecithin from egg yolk. Serva, Heidelberg, Germany, No. 27608 Lipoid S 20.

Preparation of the Emulsion 35 mg lecithin are mixed with 4.5 ml HEPES buffer (100 mmol/l, pH 7.9) and 0.250 ml 120 mmol/l taurodesoxycholate solution and stirred with gentle warming. After the lecithin is emulsified (after 80 to 110 minutes), 0.250 ml of a solution of 200 mmol/l calcium chloride dihydrate, 200 mmol/l Triton ® X-100 and 400 mmol/l magnesium chloride hexahydrate is added thereto.

Test Batch

The determinations are carried out at 37° C., measurement being made at a wavelength of 365 nm against air.

In each case, to 750 μl of the above-mentioned emulsions are added 25 μl of a CoA solution (90 mmol/l), 75 μl of a coenzyme solution (ATP: 145 mmol/l, PEP: 55 nmol/l, NADH: 9.4 mmol/l), as well as 50 μl of an enzyme solution (myokinase: 165 kU/l, LDH: 377 kU/l, PK: 141 kU/l, ACS: 5.6 kU/l). As sample, there are used 50 μl of a PLA-containing human serum.

Two of the above-mentioned lecithins are found to be suitable, namely, lecithin from soya beans (Roth 9812)

and Lipoid S 20. No PLA activity could be detected with the other lecithins using the above-described test batch.

We claim:

1. Process for the determination of phospholipase A in body fluids, comprising the steps of:
   incubating a body fluid with a mixture containing a substrate having a fatty acid residue and at least two emulsifiers of different chemical classes, where at least one emulsifier is a neutral emulsifier and at lest one emulsifier is a bile acid salt, and
   determining the amount of the free fatty acids formed by cleavage of the substrate.

2. Process according to claim 1, wherein, said substrate is lecithin from soya beans.

3. Process according to claim 2, wherein, said substrate is natural lecithin from soya beans.

4. Process according to claim 2, wherein, said substrate is Lipoid S 20 (a soy bean lecithin).

5. Process according to claim 1, wherein said substrate is a synthetic substrate of the formula I:

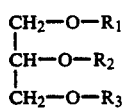

wherein $R_1$ and $R_2$ are alkyl radicals containing up to 20 carbon atoms or carbonyl radicals containing up to 20 carbon atoms, such that at least one of the two radicals is a carbonyl radical, and $R_3$ is—$SO_3H$.

6. Process according to claim 1, wherein said emulsifiers are selected from the group consisting of alkyl glucosides, polyethers, dimethyl sulphoxides, desoxycholates, and Triton ® X-100.

7. Process according to claim 6, wherein one of said emulsifiers is taurodesoxycholate.

8. Process according to claim 6, wherein said emulsifiers are octyl glucoside and taurodesoxycholate.

9. Process according to claim 6, wherein said emulsifiers are taurodesoxycholate and polyoxyethylene ether.

10. Process according to claim 6, wherein said emulsifiers are taurodesoxycholate and dimethyl sulphoxide.

11. Process according to claim 6, wherein said emulsifiers are taurodesoxycholate and Triton ® X-100.

12. Process according to claim 1, wherein said substrate is lyophilized and subsequently dissolved in a buffer.

13. Process according to claim 12, wherein said buffer is HEPES buffer.

14. Process according to claim 1, wherein the determination of said fatty acids is carried out by reaction of the fatty acids in the presence of coenzyme A and ATP with acyl-CoA synthetase to give acyl-CoA, AMP and pyrophosphate which are subsequently detected.

15. Process according to claim 14, wherein the AMP formed is detected by conversion into lactate and extinction before and after the cleavage of the substrate is measured.

16. Process according to claim 14, wherein the determination is carried out in triethanolamine hydrochloride buffer.

17. Process according to claim 14, further comprising the addition of a clarifying system which does not impair the color formation.

18. Process according to claim 17, wherein said clarification system is Triton ® X-100.

* * * * *